United States Patent [19]

Brown

[11] 4,201,566

[45] May 6, 1980

[54] METHOD OF INCREASING EXTRACTABLE OLEORESINOUS AND TALL OIL MATERIAL FROM PINE WOOD

[76] Inventor: Claud L. Brown, Rte. 2, 98 Hodges Mill Rd., Watkinsville, Ga. 30677

[21] Appl. No.: 931,169

[22] Filed: Aug. 4, 1978

[51] Int. Cl.$^2$ ............................................. A01N 5/00
[52] U.S. Cl. ............................................ 71/92; 71/94
[58] Field of Search ...................................... 71/92, 94

[56] References Cited

U.S. PATENT DOCUMENTS

| 3,839,823 | 10/1974 | Roberts et al. | 71/94 X |
|---|---|---|---|
| 3,971,159 | 7/1976 | Brown et al. | 47/10 |
| 3,991,515 | 11/1976 | Drew | 47/10 |

OTHER PUBLICATIONS

Brown et al., Forest Science, vol. 21, No. 4, (1975), pp. 359-364.
Peters et al., Abst. Lightwood Annual Meeting, p. 55, (1976), Jacksonville, Fla.
Wolter et al., Abst. Lightwood Annual Meeting, p. 31, (1976), Jacksonville, Fla.
Brown et al., Lightwood Annual Meeting Proceedings, pp. 8 to 19, (1976).
Brown-Lightwood Search Coord. Council Annual Meeting, Proceedings of-Jacksonville, Fla., (1975), pp. 30-31.
Rowe et al., as above, pp. 66, 67 and 74.
Conner et al., as above, pp. 34, 35 and 55.
Zavarin et al., as above, p. 57.
Wolter, as above, pp. 90-99.
Peters et al., as above, pp. 78-93.
Rothrock et al., Chem. Abst., vol. 85, (1976), 194315e.

*Primary Examiner*—Catherine L. Mills
*Attorney, Agent, or Firm*—Jones, Thomas & Askew

[57] ABSTRACT

A method of chemically increasing the amount of extractable oleoresinous and tall oil material from pine wood by treating severed living portions of pine trees with a dilute solution of a bipyridylium salt and storing the treated wood for a period of approximately 3 to 30 days. The living portions of pine trees may be in the form of tree boles from felled trees, stems, twigs, roots or needles and chips, shavings or sawdust thereof.

12 Claims, No Drawings

METHOD OF INCREASING EXTRACTABLE OLEORESINOUS AND TALL OIL MATERIAL FROM PINE WOOD

The present invention relates to a method of chemically increasing the amount of extractable oleoresinous material from pine wood by treating severed living portions of pine trees with a dilute solution of a bipyridylium salt and storing the treated wood for approximately 3 to 30 days.

BACKGROUND OF THE INVENTION

Oleoresins, lipids and other terpenoids are natural products of growing pine trees. The majority of these compounds are synthesized within the living tree by special cells called epithelial cells which line the vertical and horizontal resin ducts. The resin produced by the epithelial cells is then secreted into the lumen of the resin ducts.

The oleoresins and tall oil derivatives find numerous applications in the manufacture of protective coatings, emulsifiers, soaps, detergents, food stuffs, plasticizers, dimer acids, lubricants, textile chemicals and others.

Heretofore, it has been shown that bipyridylium compounds can induce increased production of oleoresin material in living, standing pine trees. See, Roberts, U.S. Pat. No. 3,839,823. The living tree is typically treated with a chemical solution by applying the solution to a treatment site on the living tree. Treatment sites have been prepared by various methods, such as: removing a small section of bark to expose sapwood, making an axe cut deep enough to expose sapwood, or by boring a small downwardly sloping hole into the sapwood. See, Brown, U.S. Pat. No. 2,971,159. The purpose of these treatment sites is to permit the chemical solution to be adsorbed into the living cells of the tree. Once applied to a living tree, the chemical is mobile and may be carried to distant areas within the tree. The chemical, once absorbed into the living cells of the bark, and wood (xylem) induces the cells to produce and secret copious amounts of oleoresin into other adjacent wood fibers until the wood becomes resin or "pitch" soaked. At least some of the carbon necessary to carry out the synthesis of the oleoresins comes from sugars and other substrates ultimately produced by photosynthesis in the leaves of the living tree. In this manner, the oleoresin production of a living tree may, after a period of from six to twelve months following treatment, be increased many fold. Following the treatment period, the tree must be felled and the heavy "pitch" soaked portions are then transported to an extraction plant where the oleoresins and tall oil components are extracted from the wood using methods well known in the art.

The foregoing methods, however, have a number of disadvantages. Trees treated by previously known methods often leave the treated trees subject to attack by bark beetles, such as the Ips species, which often results in high tree mortality. This makes the practical application of the previously known methods of treatment a high risk to current forest management practices, especially throughout the Southeast.

Due to the highly toxic nature of bipyridylium salts, their wide spread use in a living forest presents dangers to humans and animals alike. Currently, the use of bipyridylium salts has not been approved by the Environmental Protection Agency for use in forests to induce oleoresin production.

Additionally, large amounts of time are usually required to treat the living trees in the forest, cut the trees, saw the trees into useable sections and transport the wood from the forest to a processing site. Therefore, the amount of labor required by some of these prior methods may make them economically unattractive.

The present invention permits the treatment of living portions of pine trees with dilute solutions of a bipyridylium salt to increase the amount of extractable oleoresinous and tall oil materials at sites where exact and precise control can be exercised over the toxic chemicals necessary to the practice of the present invention. The present invention also permits the amount of extractable oleoresinous and tall oil material to be increased during periods of storage which had heretofore resulted in reduced amounts of such materials being available for extraction. Furthermore, the present invention provides a method for increasing the extractable oleoreinous and tall oil material from woody material, such as needles twigs, and roots which had heretofore been thought of as only waste material.

It has been found that the present method permits synthesis of oleoresin and tall oil materials in the absence of current photosynthesis by utilizing the stored foods, starch, lipids and amino acids already present in the tree.

Accordingly, it is an object of the present invention to provide an improved method of chemically increasing oleoresin and tall oil production in living pine wood or other portions of the pine tree.

Another object of the present invention is to provide a method of chemically increasing the amount of extractable oleoresinous and tall oil material from living portions of pine trees.

Yet another object of the present invention is to provide a method of chemically increasing the amount of extractable oleoresinous and tall oil material from living portions of pine trees at a site removed from the forest where exact and precise control can be exercised over the toxic chemicals used in the present invention.

A further object of the present invention is to provide a method of chemically increasing the amount of extractable oleoresinous and tall oil material from living portions of pine trees such that the period of time between treatment and realization of the increased extractable oleoresin and tall oil is greatly reduced.

Another object of the present invention is to provide a method of chemically increasing the amount of extractable oleoresinous and tall oil material from living portions of pine trees which have not heretofore been useable for oleoresin and tall oil production.

These and other objects, features and advantages of the present invention will become apparent from a review of the following detailed description of the disclosed embodiment and the appended claims.

DETAILED DESCRIPTION OF THE DISCLOSED EMBODIMENT

The present invention provides a method of chemically increasing the amount of extractable oleoresinous and tall oil material in living portions of pine trees.

It has been found that when portions of pine trees, which although still alive, have been severed from a living, standing tree, are treated with the class of normally herbicidal bipyridylium (bipyridinium) salts (see U.S. Pat. No. 3,839,823), followed by a post-treatment storage time of 3 to 30 days or until the living cells expire, the amount of extractable oleoresinous material in the pine wood is increased. Examples of such treating chemicals are:

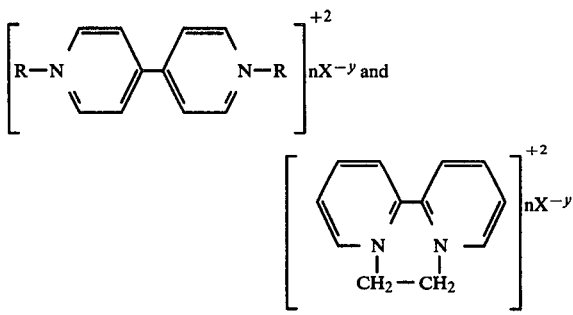

where n=1 or 2, y=1 or 2, an nxy=2 and R=CH₃—, CH₃CH₂CH₂—,

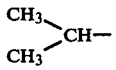

and higher aliphatic alkyl groups, either straight chain or branched; and X is any anion that makes the compound water soluble such as, but no limited to, the following:

| | |
|---|---|
| Cl | (chloride) |
| Br | (bromide) |
| F | (fluoride) |
| I | (iodide) |
| SO₄ | (sulfate) |
| NO₃ | (nitrate) |
| OH | (hydroxyl) |
| CH₃SO₄ | (methyl sulfate) |

The particularly preferred treatment chemicals for the practice of the present invention are paraquat (1,1′dimethyl - 4,4′bipyridylium dichloride) and diquat (1,1′-ethylene-2,2′bipyridylium dibromide). Solutions of the bipyridylium salt are preferably prepared as aqueous solutions, however, other solvents which are compatable with living cells of pine trees and with the bipyridylium salt may also be used.

Particular trees which may be used in conjunction with the present invention include essentially all pine species, for example: all Southern pines, *Pinus elliotti, P. echinata, P. virginiana, P. rigida, P. serotina, P. glabra;* also all northern, western and European pines.

A particular advantage of the present invention is the fact that the pine wood is not treated as a standing tree, but rather, is treated as portions of the trees, such as boles or bolts, stems, twigs, roots, foliage and the like. Moreover, it is particularly desirable in the practice of the present invention that the aforementioned tree portions be converted to chips, shavings, sawdust or the like. In the case of wood chips, it is found that a chip size produced by a conventional pulp chipper, approximately ⅛ to ¼ inch thick×1 inch wide×1—1 ½ inches long, is a useful size for accepting the chemical treatment. In the case of wood shavings or saw-dust, it is found that the thinner material permits more rapid penetraton of the bipyridylium salt into the living parenchyma cells. The increased penetration of the bipyridylium salt solution into the living cells of thinner material permits the use of more dilute solutions of the bipyridylium salt useful in the present invention. Additionally, surface active agents known in the art may be added to the bipyridylium salt solution to increase the penetration of the solution into the woody material. Generally, since the tree portions must contain living cells in order to carry out oleoresin and tall oil synthesis, it is desirable that the tree portions be as fresh as possible. Living cells generally start to senesce in felled trees, twigs, stems and the like rather quickly, with living cells of roots being somewhat slower. Generally, it is found that pine wood material which has been severed from a living, standing tree within approximately 1 to 30 days or somewhat longer, depending upon storage conditions, is useful in the present invention.

The manner of treatment of the pine wood material will, of course, vary depending on the particular form of the woody material. When small, thin pieces of woody material, such as branches, twigs, or chips are treated, a useful technique is to merely dip the pieces of woody material into a vat of the treatment chemical. When larger pieces of woody material are treated, such as an entire tree bole or a small tree bolt (pulpwood size bolts are usually of a standard 60 inches in length) they may be perfused with a pressure rig attached at either end without debarking the bole or bolt; or by debarking the bolt or bole followed by pressure treatment (either vat or tank) using conventional methods known in the art for pressure treating timbers, poles and the like for wood perservation. Other methods of treatment useful in the present invention include, for example, spraying and vacuum treatment.

When large pieces of woody material are treated, it should be understood that they must be converted into chips or the like following the chemical treatment and storage period in order to be in a useable form for extraction of the oleoresin and tall oil.

Concentrations of the bipyridylium salt useful in the treatment step of the present invention are such that the living cells in the tree portions are not killed outright by the treatment. Generally, it is found that concentrations of approximately 0.001% to 6%, preferably 0.01% to 1%, may be used.

Generally, the length of time of treatment of the pine wood material with the bipyridylium salt solution will vary depending on the size of the material being treated, i.e., whether, for example, a stem, or chip or a shaving is being treated, and whether or not the material is being treated under pressure. For a soaking treatment of conventional chip size material at ambient pressures, treatment times range from a simple dip in the treating solution to soaking the material for 60 minutes. It is found that a soak treatment of from approximately one to five minutes produces the best results in wood chips and is therefore preferable.

An essential step of the present invention is that the pine wood material must be stored under aerobic conditions for a period of time following the chemical treatment step before the increased amount of oleoresinous and tall oil material may be extracted. This post-treatment storage period is necessary in order to permit the living cells to carry out oleoresin, tall oil and lipid synthesis from the stored starch and other food reserves in the living cells. Since this synthesis is carried out by living cells which respire, it is necessary that the cells be permitted to communicate with an oxygen-containing atmosphere during the post-treatment storage period. Generally, storage periods useful in the present invention range from approximately 3 to 30 days, preferably 3 to 21 days, most preferably 14 days. These storage periods are found to be sufficient in most cases to permit the amount of extractable oleoresinous and tall oil material to be increased.

It is found that when storage periods of over approximately 10-14 days are used bacteria and fungi often develop on the woody material. This bacterial and fungal growth causes premature deterioration and death of the living wood cells. Typical fungal growths encountered include, for example, *Ceratocystis Spp.*, blue stain fungi. Therefore, in order to minimize such bacterial and fungal growths, shorter storage periods are preferred. However, when storage periods in excess of 10 days are necessary, it is possible to incorporate a fungicide, such as Benomyl, to retard undesirable bacterial and fungal growth.

It should be noted that the time between treatment and realization of increased extractable oleoresinous and tall oil material is significantly shorter than any other prior art method of treatment of standing timber. This gives the method of the present invention a considerable economic advantage over prior methods.

Following the post-treatment storage period, the oleoresinous and tall oil material is extracted from the treated pine wood material. Many methods for extracting such material are known in the art and include, for example, grinding the wood material, treatment with a suitable solvent for the oleoresin and tall oil, such as ether, alcohol, benzene, and then filtering and distilling the filtrate to obtain the crude oleoresinous and tall oil material.

In a typical commercial extraction processes, the wood is typically ground to about the size of a paper match. Alternately, in some kraft pulping process the chips are slightly larger; approximately ¼ inch × 1 inch-×1—1 ½ inches. Oleoresinous and tall oil material is then extracted from the ground wood in a vertical cylindrical extractor using a hydrocarbon solvent. Extractors are often arranged in series so that each charge of new chips is extracted by several portions of solvent in succession. Solvent remaining in the wood is removed by steam extraction, and the extract containing the oleoresinous and tall oil material is fractionally distilled to separate the products. Such a method is useful in conjunction with the practice of the present invention.

The following examples are illustrative of the present invention. In this specification, all temperatures are in degrees centigrade, all parts are parts by weight, and all percentages are weight percentages unless otherwise expressly indicated. All woody material used in the following examples were treated within one to two hours after being severed from the tree.

EXAMPLE 1

Three aqueous solutions of 1,1' dimethyl-4,4' bipyridylium dichloride having concentrations of 0.01%, 0.1% and 1.0% respectively were prepared. Individual samples of needles, current year twigs and Xylem taken from three, five-year-old slash pine trees were treated with the various concentrations of bipyridylium salt. The samples were placed in the treating solution and then placed in a vacuum jar. The pressure in the jar was reduced to 22 centimeters of mercury and the samples were permitted to soak in the solution for one minute. Pressure in the jar was then restored to ambient atmospheric conditions and the samples were permitted to soak for one additional minute. The samples were then removed from the jar, drained on paper towels, placed in polyethylene bags and stored in the dark at 25° C. for 7 days. Untreated control samples of the same material were similarly stored under the same condition. At the end of the 7 day post-treatment storage period, the samples and control samples were removed from the bags, dried at 70° C. for 24 hours, ground to pass 40 mesh screen and extracted with diethyl ether. The ether was then distilled from the extract leaving a quantity of oleoresinous and tall oil material.

The results of the test are summarized below:

| Material | Concentration of Treating Solution | Per Cent Extractives (dry-wt) | Per Cent Increase Over Control |
| --- | --- | --- | --- |
| Needles (cut 1.0cm) | 0.01 | 5.6 | +9.8 |
|  | 0.1 | 5.6 | +9.8 |
|  | 1.0 | 5.5 | +7.8 |
|  | Control | 5.1 | — |
| Twigs Chip | 0.01 | 6.2 | +6.9 |
|  | 0.1 | 6.8 | +17.0 |
|  | 1.0 | 8.2 | +41.3 |
|  | Control | 5.8 | — |
| Wood Chip | 0.01 | 3.8 | +18.7 |
|  | 0.1 | 4.0 | +25.0 |
|  | 1.0 | 3.9 | +21.9 |
|  | Control | 3.2 | — |

An increase in the amount of extractable oleoresinous material over the control sample, which was not treated with the bipyridylium solution, is found in all samples and all varieties of material.

EXAMPLE 2

Four aqueous solutions of 1,1' dimethyl-4, 4' bipyridylium dichloride having concentrations of 0.1%, 1.0%, 3.0% and 6.0% respectively were prepared. Individual samples of twigs (without leaves) and wood chips from three five-year-old slash pine trees were treated with the various concentrations of bipyridylium salt. The samples were soaked in the treating solutions for periods of either five minutes or one hour. The samples were then removed from the solution, drained on a paper towel for five minutes, placed in polyethylene bags and stored in the dark at 25° C. for 14 days. Untreated control samples of the same material were similarly stored under the same conditions. At the end of the 14 day post-treatment storage period, the samples and control samples were removed from the bags, dried at 70° C. for 24 hours, ground to pass 40 mesh screen and extracted with diethyl ether. The ether was then distilled from the extract leaving a quantity of oleoresinous and tall oil material.

The results of the test are summarized below:

| Material | Concentration of Treating Solution | Time (min) | Per Cent Extractives (dry wt) | Per Cent Increase Over Control |
| --- | --- | --- | --- | --- |
| Wood Chips | Control | 60 | 5.6 | — |
| " | 0.1 | 60 | 5.6 | 0 |
| " | 1.0 | 60 | 6.2 | +10.7 |
| " | 3.0 | 60 | 6.5 | +16.1 |
| " | 6.0 | 60 | 5.7 | +1.8 |
| Twig Chips | Control | 5 | 6.4 | — |
| " | 0.1 | 5 | 8.7 | +35.0 |
| " | 1.0 | 5 | 6.6 | +3.1 |
| " | 3.0 | 5 | 7.4 | +15.6 |
| " | 6.0 | 5 | 6.0 | −6.3 |

An increase in the amount of extractable oleoresinous material over the control sample, which was not treated with the bipyridylium solution, is found in all samples except the wood chips treated for one hour at a concentration of 0.1% and twigs treated for 5 minutes at a concentration of 6.0%. It is suspected that the reason for the negative yield in the last sample resulted from the high 6% concentration of bipyridylium in contact with young succulent twig wood. A 6.0% concentration of bipyridylium is lethal to exposed storage (living) cells, and the ratio of storage to dead fiber cells is higher in twigs than in older bole wood chips, hence more rapid, deleterious effects.

EXAMPLE 3

Two aqueous solutions of 1,1' dimethyl-4, 4' bipyridylium dichloride having concentrations of 0.3% and 3.0% respectively were prepared. Individual samples of twigs and wood chips were treated with the various concentrations of bipyridylium salt by soaking for 5 minutes. The samples were then drained on a paper towel, placed in polyethylene bags and stored in the dark at 25° C. for either 3 days or 7 days. Untreated control samples of the woody material were similarly stored under the same conditions. At the end of the post-treatment storage period, the samples and control samples were removed from the bags, dried at 70° C. for 24 hours, ground to pass 40 mesh screen and extracted with diethyl ether. The ether was then distilled from the extract leaving a quantity of oleoresinous and tall oil material.

The results of the test are summarized below:

| Material | Concentration of Treating Solution | Storage Time (days) | Per Cent Extractives (dry-wt) | Per Cent Increase Over Control |
|---|---|---|---|---|
| Twig Chips | 0.3% | 3 | 6.2 | +12.7 |
|  | 0.3% | 7 | 7.7 | +40.0 |
|  | 3.0% | 3 | 6.4 | +16.4 |
|  | 3.0% | 7 | 6.3 | +14.5 |
|  | control | 7 | 5.5 | — |
| Wood Chips | 0.3 | 3 | 6.4 | +8.5 |
|  | 0.3 | 7 | 7.9 | +33.8 |
|  | 3.0 | 3 | 7.5 | +27.1 |
|  | control | 7 | 5.9 | — |

An increase in the amount of extractable oleoresinous material over the control sample, which was not treated with the bipyridylium solution, is found in all samples and types of material tested.

It should be, understood, of course, that the foregoing relates only to preferred embodiments of the present invention and that numerous modifications or alterations may be made therein without departing from the spirit and the scope of the invention as set forth in the appended claims.

What is claimed is:

1. Method of chemically increasing the amount of extractable oleoresinous material, lipids and tall oils from living portions of pine trees comprising the steps of:

treating severed portions of living pine wood with a dilute solution of a substituted bipyridylium salt such that said solution penetrates said severed portions to reach living cells of said severed portions; and aerobically storing said treated wood for a period sufficient to permit the amount of oleoresinous material, lipids and tall oils to increase therein.

2. The method of claim 1, wherein said dilute solution of substituted bipyridylium salt has a concentration of from 0.001% to 6%.

3. The method of claim 2, wherein said dilute solution of substituted bipyridylium salt has a concentration of from 0.01% to 1%.

4. The method of claim 3, wherein said substituted bipyridylium salt is 1,1' dimethyl -4,4'-bipyridylium dichloride.

5. The method of claim 3, wherein said substituted bipyridylium salt is 1,1' ethylene- 2,2' bipyridylium dibromide.

6. The method of claim 1, wherein said treatment of said portions of living pine wood comprises soaking said portions of living pine wood in said solution for a period of from one second to 60 minutes.

7. The method of claim 6, wherein said period of soaking is from one minute to five minutes.

8. The method of claim 1, wherein said storage time for said treated wood is from 3 to 30 days.

9. The method of claim 1, wherein said storage time for said treated wood is from 3 to 21 days.

10. The method of claim 1 wherein said storage time for said treated wood is 14 days.

11. The method of claim 1, wherein said severed portions are chips.

12. The method of claim 1, wherein said severed portions are not thicker than approximately ¼ inch.

* * * * *